(12) United States Patent
Widmann

(10) Patent No.: US 7,680,542 B2
(45) Date of Patent: Mar. 16, 2010

(54) RADIOFREQUENCY ABLATION EPIPHYSIODESIS

(75) Inventor: Roger Widmann, Scarsdale, NY (US)

(73) Assignee: New York Society for the Ruptured and Crippled Maintaining the Hospital for Special Surgery, New York, NY (US)

( * ) Notice: Subject to any disclaimer, the term of this patent is extended or adjusted under 35 U.S.C. 154(b) by 1338 days.

(21) Appl. No.: 11/131,920

(22) Filed: May 17, 2005

(65) Prior Publication Data

US 2005/0263159 A1 Dec. 1, 2005

Related U.S. Application Data

(60) Provisional application No. 60/572,150, filed on May 17, 2004.

(51) Int. Cl.
*A61F 2/00* (2006.01)
(52) U.S. Cl. .......................... 607/101; 607/43; 607/51; 604/21
(58) Field of Classification Search ............ 606/41–50; 607/43, 51, 101–102; 604/21
See application file for complete search history.

(56) References Cited

U.S. PATENT DOCUMENTS 7,206,638 B2 * 4/2007 Dodge et al. .................. 607/43

OTHER PUBLICATIONS

Nickisch et al., Image-guided Radiofrequency Epiphysiodesis of the Rabbit Tibia, RSNA 2003, G15-664, 1 page.
Nickisch et al., Percutaneous Radiofrequency Epiphysiodesis: An Experimental Study in Rabbits, POSNA 2004, Apr. 27, 2004, 1 page.
Rosenthal et al., Percutaneous Radiofrequency Coagulation of Osteoid Osteoma Compared with Operative Treatment, JBJS, 80-A(6): 815-821, Jun. 1998.
Tillotson et al., Controlled Thermal Injury of Bone Report of a Percutaneous Technique Using Radiofrequency Electrode and Generator, investigative Radiology, 24 (11): 888-892, Nov. 1989.

* cited by examiner

*Primary Examiner*—Roy D Gibson
(74) *Attorney, Agent, or Firm*—Darby & Darby P.C.

(57) ABSTRACT

The present invention is directed to a method of treating bone length discrepancies and angular deformities in a patient in need thereof, where the method involves radiofrequency ablation epiphysiodesis of a physeal plate. Specifically, the method treats long bone discrepancies with a minimally invasive procedure. The present invention is also directed to a method of inhibiting bone growth, where the method involves exposing a physeal growth plate to radiofrequency ablation epiphysiodesis.

16 Claims, 1 Drawing Sheet

RADIOFREQUENCY ABLATION EPIPHYSIODESIS

CROSS-REFERENCE TO RELATED APPLICATIONS

This application claims priority under 35 U.S.C. §119, based on U.S. Provisional Application Ser. No. 60/572,150 filed May 17, 2004, which is hereby incorporated by reference in its entirety.

FIELD OF THE INVENTION

The present invention is directed to a method of treatment to equalize leg length discrepancy. Specifically, the invention is directed to the use of radiofrequency ablation epiphysiodesis to destroy the physeal plate in a controlled and precise fashion.

BACKGROUND OF THE INVENTION

Microwaves produced by a radiofrequency probe have been highly successful in many surgical arenas including: ablation of the trigeminal ganglion in patients with trigeminal neuralgia, removal of irritable foci of the cardiac conducting system, ablation of the cystic duct, thoracic sympathectomy, and rhizotomy for control of cancer pain. The use of radiofrequency ablation techniques is preferable because it generally does not require hospitalization, it has minor complications if any, and it is associated with a rapid convalescence.

Recent work in the field has demonstrated the efficacy of this technique in the ablation of osteoid osteomas through percutaneous placement of the radiofrequency probes (Rosenthal et al., JBJS, 80-A(6): 815-821, 1998). The same authors have described the creation of a controlled area of marrow and cortical necrosis from 0.9 cm to 1.3 cm in diameter with this technique in the femur of dogs (Tillotson et al., Invest Radio, 24:888-892, 1989).

Epiphysiodesis or destruction of the growth plate is a common treatment for leg length discrepancy or angular deformities. The operation is effective by slowing the growth rate of the longer limb through selective destruction of one or more growth plates. Traditionally, epiphysiodesis has been achieved by mechanical obliteration of the growth plate cartilage (physis). The purpose of the surgery is to ablate the central portion of the physis, and with subsequent healing, to produce a bony bridge that tethers the physis and prevents further growth.

Current techniques used for epiphysiodesis involve opening cortical windows on both the lateral and medial sides of the bone adjacent to the growth plate. The growth plate is manually destroyed with curettes and drills. Generally, at least 50% of the growth plate must be removed symmetrically on both sides to maximize growth arrest. As the growth plates are not perfectly flat, there are significant technical challenges to ensure that the tip of the tool is in the plate and that it stays in place throughout the procedure. Complications such as breaching the anterior or posterior cortex of the femur have potentially serious consequences with risk of vascular injury or extrusion of bone particles into the joint. Further damage to the metaphyseal region of the bone may be incurred through excessive curettage and drilling.

Therefore, there is a need for a reliable and precise procedure which overcomes the complications in the prior art. The present invention addresses this need with the use of radiofrequency ablation.

SUMMARY OF THE INVENTION

The present invention provides a new method for performing epiphysiodesis with the implementation of radiofrequency ablation. The radiofrequency probe make possible predictable areas of tissue necrosis so that the physeal plate can be destroyed in a controlled and precise fashion.

In a preferred embodiment, the target bone is a long bone. Possible target bones include the femur, tibia, humerus, radius, and ulna. Preferably, the target bone growth plate is the tibial physis.

The method of the invention is practiced in patients in need of epiphysiodesis. In one embodiment, the patient is human. In a preferred embodiment, the patient is a pediatric patient. In another embodiment, patient is an animal.

In a specific embodiment, the method involves the following steps:

(a) identifying a target bone growth plate site;
(b) making at least one percutaneous incision at the target site;
(c) inserting a guide wire into the incision site transversely into physeal cartilage at the target site to create a channel;
(d) inserting a radiofrequency electrode probe into the channel, wherein the probe is connected to a radiofrequency generator;
(e) heating the probe to ablate the target site for a set duration of time;
(f) removing the probe; and
(g) surgically closing the incision.

Preferably, the method is achieved with a percutaneous approach, decreasing the invasiveness and morbidity associated with traditional techniques. The incision length ranges from about 0.2 cm to about 3 cm, preferably from about 0.3 cm to 1.0 cm, more preferably from about 0.02 mm to about 10 mm. The incision is preferably closed with sutures.

In one embodiment, the radiofrequency electrode probe used in to ablate the target site ranges in diameter fro about 0.4 mm to about 1 mm. In one embodiment, the probe is heated to about 50° to about 100° C., preferably heated from about 70° to about 90° C. The duration of exposure ranges from about 1 second to about 10 minutes, preferably from about 1 minute to about 5 minutes.

The invention is also directed to a method of inhibiting bone growth no a bone in need of such treatment, where the physeal growth plate is exposed to radiofrequency ablation epiphysiodesis.

DETAILED DESCRIPTION

Figure 1:
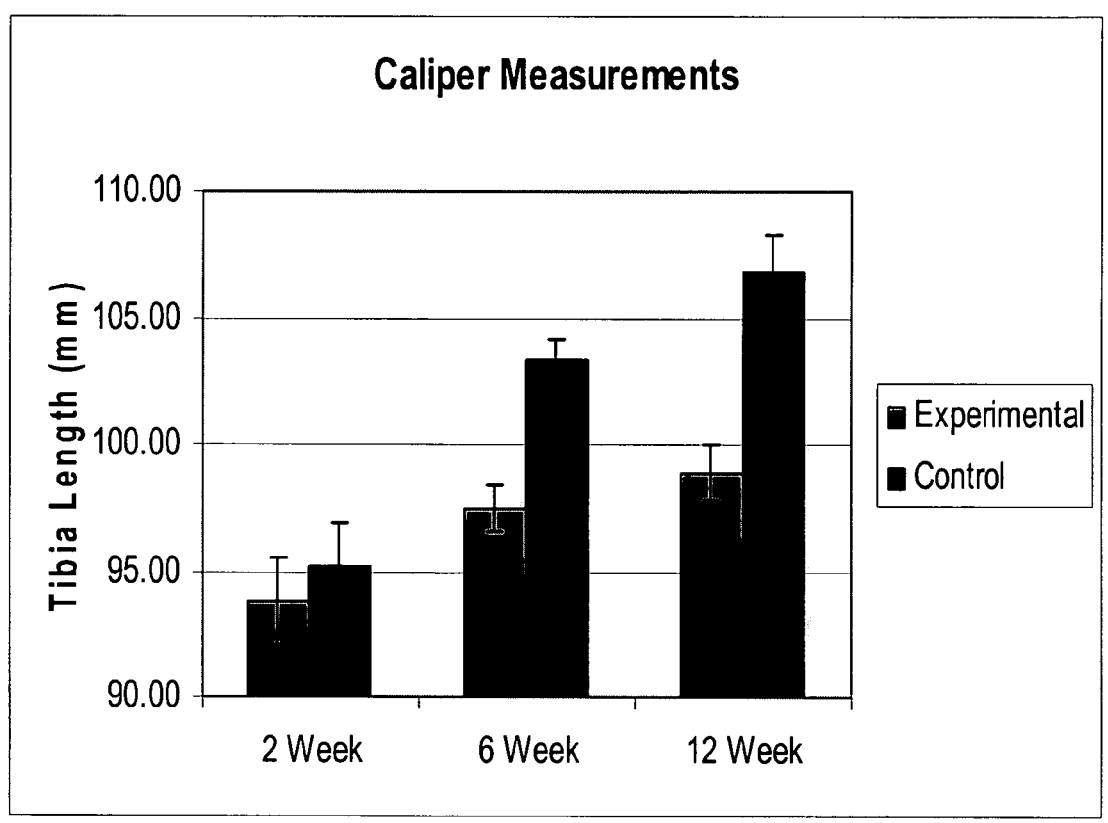
FIG. 1 depicts a graphical representation of the tibia length caliper measurements in mm of the control and experimental groups at 2 weeks, 6 weeks, and 12 weeks.

The present invention utilizes the techniques of radiofrequency ablation to achieve epiphysiodesis through a minimally invasive procedure.

The method of the invention requires a percutaneous incision to be made at the target site. In a preferred embodiment, this target site is at a bone growth plate. This site may be any long bone including for example the femur, tibia, humerus, radius and ulna. Other applications include epiphysiodesis of metacarpals, metatarsals and the phalanges of the upper and lower extremities. In one embodiment, the target site is the tibial physis. The location of the growth plate is confirmed by way of fluoroscopic radiographic imaging.

One or more percutaneous incisions may be necessary to locate the target site. If the tibial physis is the target, then lateral and medial incisions are made directly over the growth plates of the proximal tibia. The incision length is dependent upon the target area. However, the incision length is kept conservative and is intended to minimize invasiveness. In one embodiment, incision length ranges from about 0.2 to about 3 cm, preferably from about 0.3 to about 1.0 cm.

Once the location of the bone growth plate is confirmed, a guide wire is inserted transversely into the physeal cartilage at the target site. If more than one incision is made, for example, for the proximal tibia, then a guide wire is inserted to form a channel from both the lateral and medial directions. In one embodiment, a Kirshner wire exactly the same size or slightly larger than the diameter of the radiofrequency probe is used. In one embodiment of the invention, the diameter of the probe ranges from about 0.02 mm to about 10 mm. Preferably, the diameter of the probe ranges from about 0.02 mm to about 2 mm, more preferably from about 0.4 to about 1 mm.

A radiofrequency electrode probe is advanced through the hole made by the Kirshner wire. The radiofrequency electrode is used with a radiofrequency generator to heat the tip of the electrode within the bone growth plate. In one embodiment, a Radionics radiofrequency generator (Radionics, Inc., Burlington, Mass.) with a Radionics SMK-10 probe (Radionics, Inc., Burlington, Mass.), and a Radionics reusable probe cannula are used. These particular devices have been successfully utilized in a rabbit model. For larger animal or human use, larger diameter probes are more appropriate.

Grounding pads are utilized, and temperature, duration, and current of the electrode are controlled to ensure sufficient tissue necrosis. The temperature of the electrode ranges from about 50° C. to about 100° C., preferably from about 70° C. to about 90° C. The duration of exposure to the heated electrode ranges from about 1 second to about 10 minutes, preferably from about 1 minute to about 5 minutes. For example, in experiments on a rabbit physeal plate, heating the electrode to 90° C. for 4 minutes was sufficient to destroy the physeal plate and achieve an epiphysiodesis effect. The electrode is moved and reheated to cover the entire area of the physis.

Upon completion of the ablation procedure, the electrode is removed, and the incision wound is surgically closed with sutures. Preferably, the sutures are absorbable. However, in another embodiment, the sutures are removable.

In one embodiment, the procedure is used to treat leg length discrepancies. In another embodiment, the procedure is used to treat angular deformities. However, the procedure may be extended to other bones including upper limb discrepancies, depending on the bone length discrepancy, and other bone related conditions. This technique is applicable to any long bone with an open growth plate and to limb length discrepancy of any etiology.

The method of the present invention is intended for use in patients in need of such treatment. In a preferred embodiment, the patient is human, preferably a pediatric patient. In an alternative embodiment, the procedure may be used in animals.

The term "about" or "approximately" means within an acceptable error range for the particular value as determined by one of ordinary skill in the art, which will depend in part on how the value is measured or determined, i.e., the limitations of the measurement system. For example, "about" can mean within 1 or more than 1 standard deviations, per the practice in the art. Alternatively, "about" can mean a range of up to 20%, preferably up to 10%, more preferably up to 5%, and more preferably still up to 1% of a given value. Alternatively, particularly with respect to biological systems or processes, the term can mean within an order of magnitude, preferably within 5-fold, and more preferably within 2-fold, of a value.

EXAMPLES

The present invention will be better understood by reference to the following Examples which are provided as exemplary of the invention, and not by way of limitation.

Example 1

Radiofrequency Ablation Epiphysiodesis in Rabbits

The present example demonstrates the effect of radiofrequency ablation on a living, growing growth plate.

Methods

The procedure was a minimally invasive technique on an animal model using male New Zealand white rabbits. Fifteen twelve-week old (skeletally immature) rabbits were divided into the following three experimental groups as shown in Table 1.

TABLE 1

|  | Age of Rabbits (weeks) | Number of Rabbits | Time of Sacrifice (weeks) |
| --- | --- | --- | --- |
| Group I | 12 | 5 | 2 |
| Group II | 12 | 5 | 6 |
| Group III | 12 | 5 | 12 |
| Total | — | 15 | — |

Only male rabbits were used to rule out the factor of the gender on the size of the animal.

By 12 weeks of age, the rabbit tibia achieves 82% of its adult length. By 20 weeks of age, 98% of the adult tibia length is attained. The proximal tibia was chosen because it has a relative flat physis that facilitates surgical manipulation as compared with the undulating shape of the distal femoral physis. Additionally, radiographs of the tibia can be measured more accurately since magnification errors are minimized by positioning. Both tibias of each rabbit are used. One side is designated the control group where the other side is the experimental side upon which the radiofrequency procedure are performed. By using both sides of each rabbit, each animal serves as its own control.

Power of the study was calculated according to Rosen et al. (Clin Orthop 1990, 256:244-253). The expected minimum difference to detect is as significant as 3 mm and the estimated standard deviation of each population, 1.5 mm.

Each rabbit was prepped and draped in a standard surgical fashion as follows. Rabbits received no food, water only, for 12 hours prior to surgery. Hind paws were covered with moisture-proof material and suspended, to prevent contamination of surgical site. The distal femur and proximal tibia with wide margins (10 cm or more if possible) were clipped free of hair, and scrubbed twice with betadine soap, then wiped with 70% isopropyl alcohol. The final scrub was performed by the surgeons in the operating room.

Two medial incisions (less than 1 cm) were extended directly over the growth plates of the proximal tibia of both rabbit hind-legs after general endotracheal anesthesia. Anesthetic induction was achieved with ketamine hydrochloride 35-60 mg/kg, combined with acetylpromazine 0.5 mg/kg in a single syringe and was administered subcutaneously. 0.05 mg/kg atropine was added, if necessary. If additional relaxation is required for catheterization or intubation, diazepam, 1-2 mg/kg intravenously may be administered. The endotracheal tube was inserted, tested for correct placement, secured to head, and the cuff inflated.

Prophylactic antibiotic of ampicillin 25 mg/kg intramuscularly or subcutaneously was administered. A lateral auricular vein, butterfly catheter (23 or 25 g) was placed aseptically and taped securely. Anesthesia was maintained via isoflurane inhalation. ECG, pulse, breathing, anesthetic depth were monitored continually, and documented in the anesthetic record by the veterinary staff.

The location of the physis was confirmed with anteroposterior (AP) and lateral fluoroscopy using a portable fluoroscopic xray machine (OEC Medical Systems, Salt Lake City, Utah). The radiofrequency electrode was advanced through the hole. The radiofrequency electrode contains an internal thermistor for simultaneous temperature measurement, and the exposed effective length of the microwave source was 2-2.5 mm. A Radionics RF-5 (Burlington, Mass.) radiofrequency generator was used. The current was grounded by a grounding pad. After placement of the electrode, AP and lateral fluoroscopy were obtained to verify that the tip of the electrode was within the physeal plate. The radiofrequency generator was used to heat the tip of the electrode to 90° C. for 4 minutes. A zone of tissue necrosis approximately 10 mm in diameter resulted from this intervention. The electrode was then withdrawn the length of the tissue necrosis zone and a second lesion was made using the identical parameters. The procedure was repeated until the entire physis was effected. Throughout the procedure, anesthesia depth was monitored with pulse oximeter, breathing and heart rate.

At the completion of the ablation procedure, the electrode was removed, the wound was surgically closed with one or two interrupted absorbable sutures. In the control animals, the Kirshner wire was used to make a transverse hole across the physis, and the RF device was inserted but not activated.

Routine post-operative care was administered after procedures. An initial peri-operative dose of buprenorphine (0.01-0.05 mg/kg SC) was administered just before the animal was moved from the recover area and returned to home cage. The animal was fitted with an Elizabethan collar once it fully recovered from anesthesia. A second dose of buprenorphine, at the same rate, was administered during morning rounds on the following day. A third dose, at the same rate, was administered during PM check of the first post-operative afternoon. The procedure was essentially purcutaneous, allowing the animals to fully weight-bear after surgery without difficulty. There was minimal compromise to the integrity of the proximal tibia with this technique.

Post-surgical testing. At the completion of the procedure, the rabbits were sacrificed at varying time intervals according to Ross et al. (Clin. Orthop 1997, 340:236-43) as set forth in the following Table 2.

TABLE 2

| Study | Week | | | | |
|---|---|---|---|---|---|
| | 1 | 2 | 6 | 12 | 20 |
| Epiphysiodesis | X | | | | |
| Sacrifice of rabbits | | X (first group) | X (second group) | X (third group) | |
| Gross examination | X | X | X | X | |
| Radiological examination at sacrifice | X | X | X | X | |

TABLE 2-continued

| Study | Week | | | | |
|---|---|---|---|---|---|
| | 1 | 2 | 6 | 12 | 20 |
| Histologic examination | | X | X | X | |
| Final report | | | | | X |

The first group of 5 rabbits were sacrificed at post-op week #2. The second group of 5 rabbits were sacrificed t 6 weeks, and the third group of 5 rabbits were sacrificed at post-op week #12. The length of the exploited tibias was measured following euthanasia. Euthanasia included pre-tranquilizing with acetylpromzaine, 0.4 mg/kg SC or IM or anesthetizing with Ketamine, 50 mg/kg IM. Sodium pentobarbital 100-150 ml/kg IV, via lateral auricular vein was used to sacrifice animals.

X-rays were performed on the sacrificed animals to look for radiographic evidence of tissue necrosis. Gross and histologic specimens were then examined to precisely quantify the zones of necrotic tissue resulting from the ablation procedure. Comparisons were then made between the groups. Outcome measures included tibial leg lengths discrepancy, histologic appearances and histomorphometry.

Results

At 12 weeks, average experimental tibia length was 7.86 mm shorter than average control tibia length at sacrifice ($p=0.004$). Data for tibia length is shown in Table 3 below.

TABLE 3

| | 2 Weeks (mm) | 6 Weeks (mm) | 12 Weeks (mm) |
|---|---|---|---|
| Change in Length | 1.4 | 6.1 | 7.7 |
| Range | 0.5-2.5 | 4.5-8.5 | 4.5-9.5 |
| Std. Deviation | 0.7 | 1.6 | 2.8 |
| p Value | 0.002 | 0.0009 | 0.004 |

Caliper measurements of the tibia length are shown in Table 4.

TABLE 4

| | 2 Weeks (mm) | 6 Weeks (mm) | 12 Weeks (mm) |
|---|---|---|---|
| Change in Length | 1.58 | 5.77 | 7.86 |
| Range | 0.91-2.62 | 4.18-7.07 | 4.16-9.32 |
| Std. Deviation | 0.70 | 1.07 | 2.88 |
| p Value | 0.003 | 0.0003 | 0.003 |

FIG. 1 depicts the caliper measurements of the tibia length in mm of both the control and experimental groups at 2 weeks, 6 weeks, and 12 weeks.

At two weeks, histologic assessment demonstrated destruction of 65.7 percent of the physeal width on the experimental side. The range was 39.1-100%. The control side demonstrated normal proximal tibia physeal anatomy with complete healing of the channel created by the probe. At six and twelve weeks, there was complete ablation of the growth plate. There was no articular cartilage damage as a result of the procedure.

Conclusion

This study demonstrated that percutaneous radiofrequency epiphysiodesis is an effective and reproducible method for destruction of the proximal tibia growth plate in a rabbit model. This technique may be useful for epiphysiodesis of small tubular bones of the hand and feet.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

Patents, patent applications, publications, product descriptions, and protocols are cited throughout this application, the disclosures of which are incorporated by reference herein in their entireties for all purposes.

What is claimed is:

1. A method of treating bone length discrepancy in a patient in need of such treatment, which comprises
   (a) identifying a target bone growth plate site;
   (b) making at least one percutaneous incision at the target site;
   (c) inserting a guide wire into the incision site transversely into physeal cartilage at the target site to create a channel;
   (d) inserting a radiofrequency electrode probe into the channel, wherein the probe is connected to a radiofrequency generator;
   (e) heating the probe to ablate the target site for a set duration of time;
   (f) removing the probe; and
   (g) surgically closing the incision; wherein a physeal growth plate on a bone in need of such treatment is destroyed using radiofrequency ablation epiphysiodesis.

2. The method of claim 1, wherein the bone is a long bone.

3. The method of claim 2, wherein the long bone is selected from the group consisting of a femur, tibia, humerus, radius, and ulna.

4. The method of claim 1, wherein the physeal growth plate is a tibial physis.

5. The method of claim 1, wherein the patient is human.

6. The method of claim 1, wherein the patient is a pediatric patient.

7. The method of claim 1, wherein the patient is an animal.

8. The method of claim 1, wherein the incision is between about 0.2 cm and about 3 cm in length.

9. The method of claim 1, wherein the incision is between about 0.3 cm and 1.0 cm in length.

10. The method of claim 1, wherein the probe is between about 0.02 mm and about 10 mm in diameter.

11. The method of claim 1, wherein the probe is between about 0.4 mm and about 1 mm in diameter.

12. The method of claim 1, which comprises heating the probe to between about 50° and about 100° C.

13. The method of claim 1, which comprises heating the probe to between about 70° and about 90° C.

14. The method of claim 1, which comprises exposing said bone plate to said radiofrequency for between about 1 second and about 10 minutes.

15. The method of claim 1, which comprises exposing said bone plate to said radiofrequency for between about 1 minute and about 5 minutes.

16. The method of claim 1, which comprises closing the incision with sutures.

* * * * *